United States Patent [19]

Hertzberg et al.

[11] 4,053,776

[45] Oct. 11, 1977

[54] SUB-MICRON PARTICLE DETECTOR

[75] Inventors: Martin Hertzberg; Charles D. Litton, both of Pittsburgh; Randall Garloff, Monroeville, all of Pa.

[73] Assignee: The United States of America as represented by theSecretary of the Interior, Washington, D.C.

[21] Appl. No.: 689,757

[22] Filed: May 25, 1976

[51] Int. Cl.$^2$ ............................................. G01T 1/185
[52] U.S. Cl. .................................... 250/382; 250/384; 340/237 S
[58] Field of Search ............... 250/379, 375, 380, 381, 250/382, 384, 389, 395; 324/33; 340/237 S

[56] References Cited

U.S. PATENT DOCUMENTS

| 3,521,263 | 7/1970 | Lampart et al. | 250/384 X |
| 3,573,460 | 4/1971 | Skala | 250/383 X |
| 3,735,138 | 5/1973 | Rork et al. | 250/375 |

Primary Examiner—Archie R. Borchelt

Attorney, Agent, or Firm—Thomas Zack; Donald A. Gardiner

[57] ABSTRACT

An instrument to detect submicron particles by charge-transfer attachment. The instrument is made up of a charging chamber with two concentric cylindrical electrodes, a remote third collector electrode, and a pump to force ambient air through the charging chamber and into the collection electrode. The innermost electrode of the charging chamber is supplied with a radioactive material having a gold foil covering. This material can create a small bipolar region symmetrical to the inner electrode where primary ionization takes place. Positive ions created in this region move to the larger outside unipolar region to attach themselves to submicron particles. These charged particles are then forced from the charged chamber at which time they may either impinge on the collection electrode to create a measurable axial current or the particles may enter a size discrimination chamber. Should they enter this discrimination chamber, particles of a given mobility or size are collected by two additional concentric cylindrical electrodes.

10 Claims, 5 Drawing Figures

SUB-MICRON PARTICLE DETECTOR

BACKGROUND OF THE INVENTION

Field of the Invention

This invention is a combined improved fire detector, incipient combustion detector and/or a particulate pollution monitor.

DESCRIPTION OF THE PRIOR ART

Two basic smoke detection methods are currently available to detect a fire in its incipient stage. These smoke detectors usually operate by optical scattering or attenuation (optical smoke detectors) or by the reduction of an ionization current generated by a radioactive source (ionization smoke detector). Our invention is an improved detector which utilizes the basic principles of the ionization smoke detector but overcomes several of its major drawbacks - its insensitivity to certain types of plastic smokes and its false responses to high flow velocities, or variations in ambient air composition. This invention was specifically designed to be as independent as possible of the gas flow velocity within the environment in which the instrument is placed.

A typical prior art patent reference is that to T. Lampart et al bearing U.S. Pat. No. 3,521,263. Therein a diode type ionization chamber with an ion producing inner radiation electrode source 2 is disclosed and so arranged that it is surrounded by a second outer electrode 1 (FIG. 4, column 5, lines 43-64). The sensitivity of the device relates to the residence time of the primary ions which is maximized by using low electric fields everywhere within the diode. Because these fields may be too low there may be a recombination of primary positive and negative ions to reduce the sensitivity of the device.

Our invention distinguishes over Lambert and similar references by (1) having a cylindrically symmetrical region of primary ionization; (2) having a high electric field in the bipolar ion region together with a broad and large region of unipolar ions of low electric field to maximize the residence time of those ions whose charge we wish to transfer to the submicron particles; (3) controlling the flow and charging of smoke particles in the unipolar region; (4) collecting the flow of these charged particles as a secondary current which can accurately be measured; (5) comparing the magnitude of the secondary current to the reduction in primary current caused by the charge transfer; and (6) analyzing the secondary current to determine sub-micron particle size distributions.

SUMMARY OF THE INVENTION

The triode detector forming the subject of this invention has a gas tight housing enclosing a charging chamber with an inner and outer electrode arranged as two generally concentric cylindrical electrodes. To achieve a symmetrical bipolar charge region near the inner electrode, this electrode has a radioactive source with a covering to limit the effective travel distance of emitted radioactive particles. Remote from this chamber is a third electrode used to collect a secondary current when charged particles impinge thereon. Circuitry is provided to measure this secondary current which relays the desired information on the detected particles. There is also a pump system to move ambient air into the chamber and to the collection electrode.

The primary object of this invention is an improved triode submicron particle detector.

This invention was primarily designed to detect fires at the earliest possible stage. During the incipient stage of a fire, as well as all later stages, large densities of submicron particles are generated by virtually all combustible materials. Tested materials have included coal, wood, cellulose, tobacco, polyvinyl chloride, and neoprene. Our invention detects the presence of the generated submicron particles and may, with an added feature, discriminate between those detected particles according to their size. Although our primary concern in designing this detector was to detect fires in their incipient stages, particularly in environments like coal mines, its use is not so limited. It may be used as a particulate pollution monitor or as a detector for any type of submicron particle. By submicron particles we mean particles whose largest dimension is in the $10^{-5}$ centimeter (cm) size or smaller.

The basic theory of the invention is to charge a submicron particle by passing it through a unipolar ion cloud. The cloud is generated by a radioactive source incorporated into a center electrode and an electric field between the center electrode and an outer, concentric, cylindrically shaped second electrode. This unipolar ion cloud covers most of the annular space between the center electrode and the outer electrode except for the narrow region immediately around the center electrode which is a bipolar region of primary ionization. Radioactive material is uniformly incorporated into the center electrode by being embedded therein along its length to insure that the area of primary ionization is generally cylindrically symmetrical. A gold foil of controlled thickness surrounds the source to insure that the region of primary ionization occurs close to the center electrode.

Figure 1:
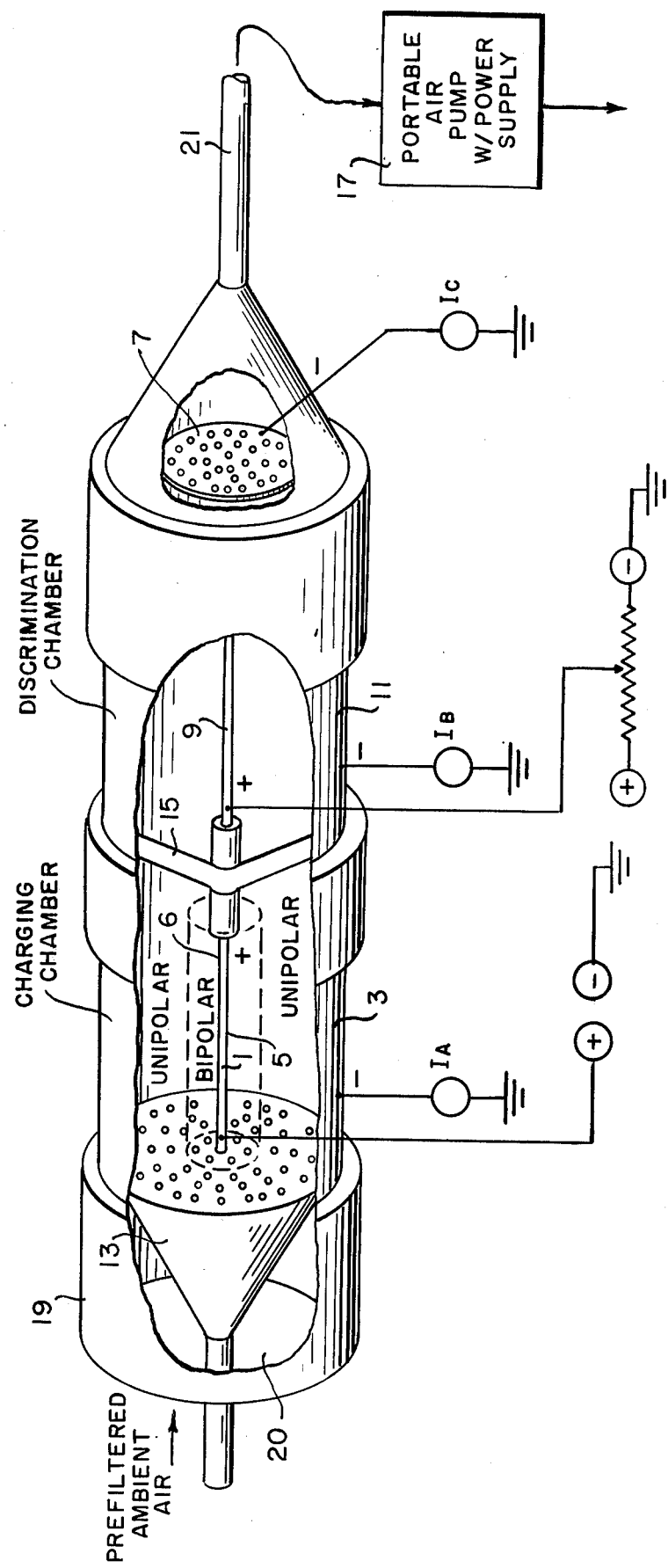
FIG. 1 is a schematic diagram, shown with the outer housing cut away specific areas, of the preferred embodiment of the detector.

Initially a positive potential is applied to the center electrode 1 as prefiltered submicron particles from the ambient atmosphere enter the chamber from the left in the direction of the arrow shown in FIG. 1. The cylindrical concentric outer electrode 3 is meanwhile held at zero potential. From radioactive material 5, coextensive with the center electrode surrounded or coated with gold foil 6, emitted alpha particles travel a small distance into space to form the bipolar region. Americium 241 or a similar radioactive material may be used for this purpose. These emitted alpha particles create electrons which attach to neutral molecules to become negative ions and they also create positive ions. Because of the potentials applied to the electrodes, the negative ions will be attracted towards the center electrode 1 and the positive ions towards the outer electrode. Since, the unipolar cloud is much larger in volume than the bipolar cloud by design, most submicron particles will acquire a positive charge as they travel through the cloud. Currently we have tried to keep the bipolar region to less than five percent of the total charging chamber volume thereby allowing the remaining ninety five percent or more to be occupied by the unipolar region. After becoming charged, the positively charged particles are attracted to the collection electrode 7 which is maintained at or near zero potential. It is here that an electric current signal is normally transmitted to an observer, which current is proportional to the concentration of smoke particles in the ambient atmosphere.

In the FIG. 1 preferred embodiment a size discrimination chamber has been added to the basic invention. It is downstream of the charging chamber, between it and the collection electrode. Like the charging chamber it is made up of two concentric cylindrical electrodes. The inner center electrode 9 is surrounded by the spaced outer electrode 11. By applying a specific electric field $E_D$ between the two electrodes all the particles less than a given size are collected within the size discrimination chamber while the particles greater than a given size are measured at the collection electrode. This fractional distribution of particle sizes may be determined by noting current readings obtained at the discrimination chamber and the collection electrode. To get these readings three ammeters Ia, Ib, and Ic are connected to the charging chamber, size discrimination chamber, and collection electrode, respectively. In this arrangement meter $I_A$ would measure the current due to primary ionization in the radial direction in the charging chamber. The readings on meter $I_B$ would represent those smoke particles below a certain size and the $I_C$ readings the smoke particles above that size. By varying $E_d$ and measuring its effect on the distribution of current between $I_B$ and $I_C$, a fractional size distribution may be obtained.

The other features shown in FIG. 1 include the tubular shaped center insulator support 15 between two chambers, the portable battery operated air pump 17, and the funnel shaped flow straightener 13 to insure laminar flow of the ambient air into the chambers and the outer solid cylindrical housing 19 of which the two outer grounded electrodes are a part. Except for the gas inlet 20 and outlet 21, to allow ambient air to enter and exit from the detector unit, the housing is air tight. Not shown are several normal dust filters to filter out particles in the $10^{-4}$ to $10^{-5}$ cm diameter range or above before they reach the inlet to the housing.

Figure 2:
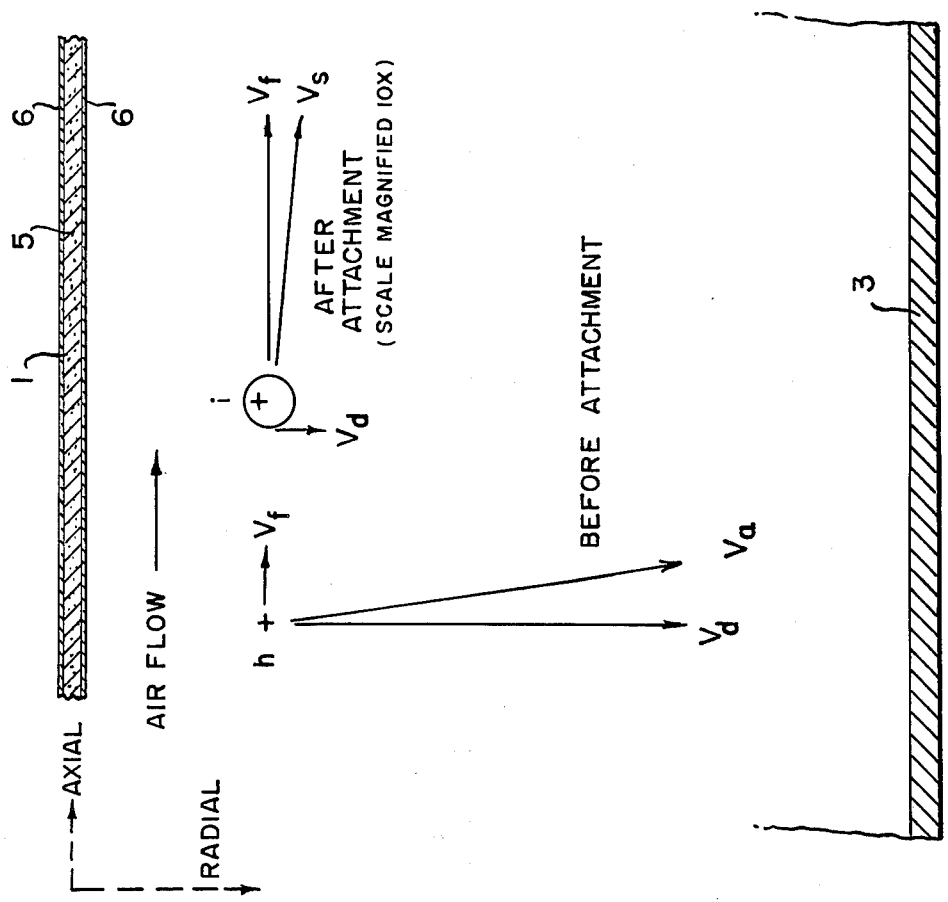
FIG. 2 is a vector diagram of the forces acting on a typical air ion and charged smoke particle as they move in or through the detector charging chamber.

FIG. 2 describes the basic forces acting on the particles while in the charging chamber. In this vector diagram $V_d$ is the drift velocity acting on the particles, $V_f$ the flow velocity, $V_a$ the resultant flow velocity of air ions, and $V_s$ the resultant flow velocity of smoke ions. As before, the outer electrode 3 is symmetrical with the center electrode 1 and its embedded radioactive source 5. The gold foil layer 6 also encircles the electrode. The letter $h$ represents the primary positive air ion flowing radially outwardly from the center electrode and the letter $i$ the secondary smoke ion flowing axially upward. The axial and radial directions are oriented as shown. For ease in depiction the smoke particle's velocity vectors have been magnified ten times after attachment of the positive air ion. The flow of primary air ions of high mobility is mainly radial in direction and is controlled by their drift velocity in the radial electric field. After ion attachment the secondary smoke ions have a much lower mobility and follow the axial gas flow.

Figure 3:
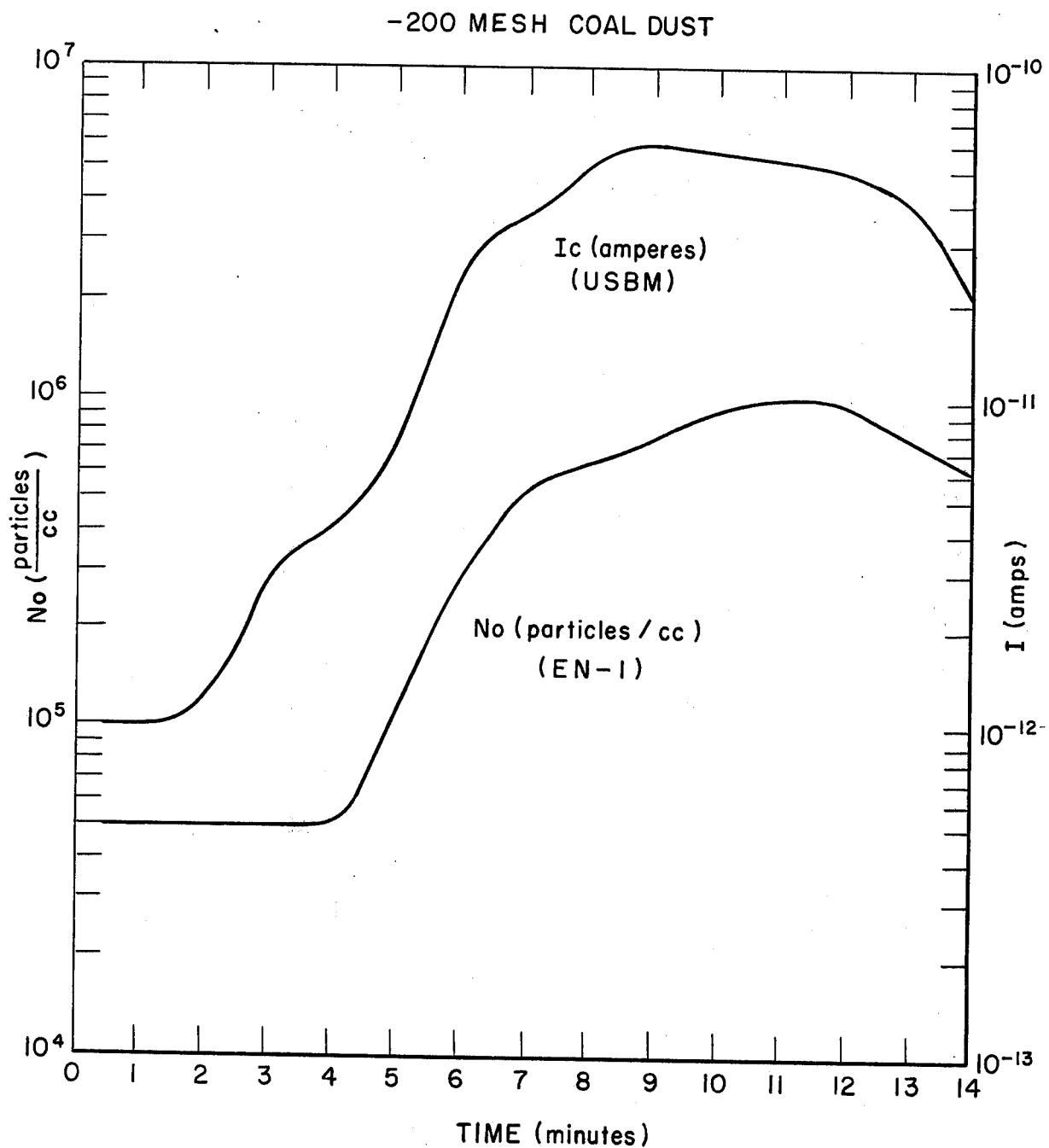
FIG. 3 is a graph taken at the collection electrode illustrating the performance of the typical Wilson cloud chamber smoke detector as contrasted against an embodiment of this invention.

FIG. 3 compares the responsivity of this triode detector invention - without the size discrimination chamber — to that of a Wilson Cloud chamber Detector manufactured by the Environment One (EN-1) Corp. of Schenectady, N.Y. Our invention is represented by the graph with the U.S. Bureau of Mines (USBM) label. The data points were plotted against heating time in minutes. All results were calibrated against 200 mesh coal pyrolyzing on a hot plate.

For various particulate sources, the average charge per particle will vary because of the differing size distributions. For three different sources, the following table illustrates the variation in measured figure of merit with volumetric flow rate.

TABLE I

| $q_v$ (Liters/min) | $\dfrac{I_c}{N_o}$ (Matches) | $\dfrac{I_c}{N_o}$ (Tobacco) | $\dfrac{I_c}{N_o}$ (Paper) |
|---|---|---|---|
| .5 | $1.2 \times 15^{-17}$ | | |
| 1.0 | $1.65 \times 10^{-17}$ | | $1.77 \times 10^{-17}$ |
| 2.0 | $3.80 \times 15^{-17}$ | $1.3 \times 10^{-16}$ | $3.4 \times 15^{-17}$ |
| 2.9 | | | $3.75 \times 10^{-17}$ |
| 8.0 | | $2.0 \times 10^{-16}$ | |

Where $q_v$ is the volumetric gas flow, $N_O$ the number of particles per cubic centimeter, and IC the measured current. The results indicate that, indeed, the sensitivity of the instrument increases with increasing flow rate. In any practical application, however, the flow rate will be limited by the capacity of the pump and the volume of the instrument.

FIG. 3 shows a direct correlation between the particle density as measured with the EN-1 and the current at the collection electrode of our invention. The more dense the concentration of particles, as detected by the EN-1 unit, the more current will be collected on our unit. Conversely, decreases in particulate density will result in less current at the collector.

Figure 4:
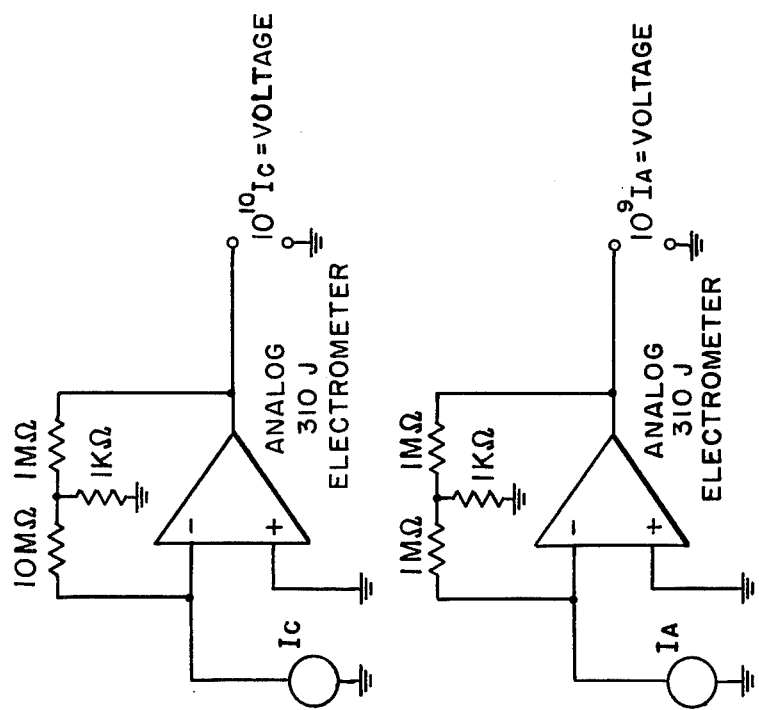
FIG. 4 depicts the circuitry used for the ammeters of FIG. 1, which detect the primary air current and secondary smoke current.

To measure the primary ionization (ammeter $I_A$) and secondary smoke current (ammeter $I_C$) two similar types of circuit arrangemtns using Analog 310 J electrometers manufactured by Analog Devices, Inc. of Cambridge, Mass. were employed as depicted in FIG. 4. Except for the fact that one feedback resistor to the smoke detector is ten times larger in ohmic value (10 million ohms versus 1 million ohms), both circuits are the same. These same circuits with certain modifications could also be used for measuring the current ($I_B$) in the size discrimination chamber.

Figure 5:
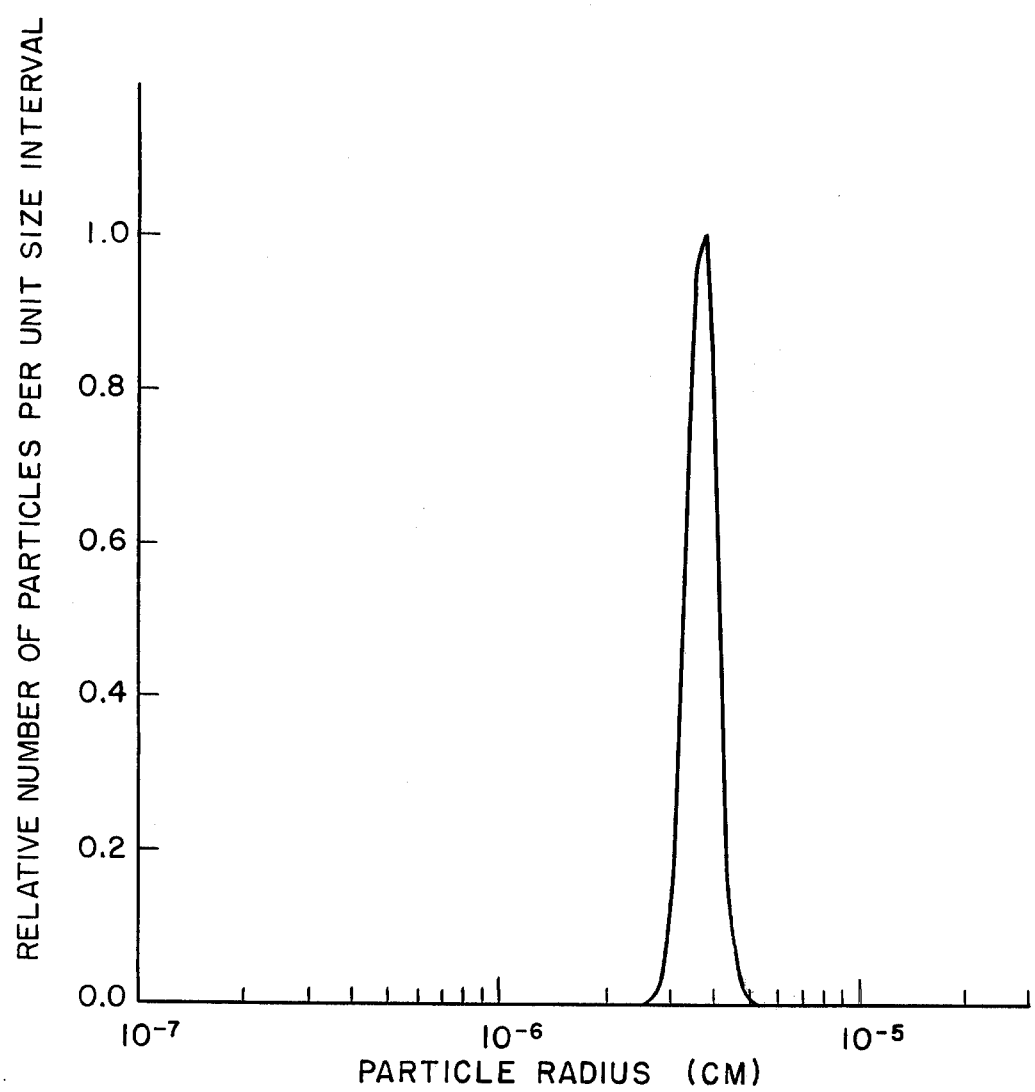
FIG. 5 is a graph illustrating the performance of the size distribution chamber.

FIG. 5 is a graph illustrating the performance of the size discrimination chamber. The relative number of particles within each size interval is shown as a function of particle radius for smoke particles generated from alpha cellulose undergoing low temperature pyrolysis. As can be seen, the average particle radius is approximately $4 \times 10^{-6}$ cm (400 A). The ordinate was calculated from the distribution of total particle current ($I_B/I_B + I_C$), and the abscissa was calculated from the voltage difference between electrodes 9 and 11. At low voltages smaller particles are collected at electrode 11, while at higher voltages larger particles are also collected. FIG. 5 is the mathematical derivative of the total current vs. voltage curve, and thus represents the size distribution of the collected particles.

One of the most important features of this invention is the construction of the charging chamber's center electrode. The radioactive material 5 is uniformly embedded in and along the total length of the electrode 1. When Americium 241 was choosen as the radioactive alpha particle emitter these particles would, if not covered, normally ionize the air out to about 4 cm in diameter from the center electrode. By encasing the electrode with a thin (6.5 μm) gold foil coating having an almost equivalent mass area-density as 4 cm of ambient air, the effective ionization distance is decreased to about 5 millimeters (mm). This allows the unipolar ion transfer region to occupy a larger percentage of the chamber's volume thus insuring a much greater probability of charge transfer attachment to the smoke particles. In other words, it is highly desirable to make the volume where ions are created as small as possible and the transfer volume as large as possible. If no foil were used, the charging volume would be bipolar i.e., it would contain both positive and negative charges. The foil shrinks the bipolar region to a relatively small volume of the charging chamber which volume cylindrically encircles the center electrode. When a potential difference is applied between the two electrodes of the charging chamber, the positive ions created by the radioactive source drift with some net velocity toward the outer electrode held at zero potential. The negative ions are drawn towards the center electrode held at some positive potential $V_o$. By varying the thickness of the gold foil, within limits, the unipolar region is allowed to increase or decrease in volume. The following equation relates the electric field E to the voltage difference V between electrodes 1 and 3, the radial spatial distance r from the axis of the center electrode, the radius $r_a$ of the center electrode, and the outer electrode radius $r_b$:

$$E = \frac{V}{r} \frac{1}{\ln r_b/r_a} \tag{1}$$

Initially with no particulate matter present and a potential of constant valve applied, the current reading on meter $I_A$ will be constant while the readings on meters $I_B$ and $I_C$ will both be zero. As filtered particles enter the housing through the inlet and straightener, the reading of $I_A$ will drop from its initial value by the amount being transferred to the particles. Meter readings on $I_B$ and $I_C$ combined will show this drop of meter $I_A$. If the potential being applied across the discrimination chamber is initially zero then all of the transferred charge will appear as current on the collector's electrode (Ic). As the potential difference in the discrimination chamber increases more and more of the transferred particle charge will appear as a current reading on the meter $I_B$.

In one working embodiment of this invention the bipolar region extended out about 0.5 cm from the center electrode and the diameter of the cylinder 19 was about 2 inches wide. The total length of the detector was about 18 inches, the charging chamber was maintained at a fixed potential difference of 245 volts with a positive center electrode, the discrimination chamber potential varied between 0 to 2,500 volts, and the collector electrode was kept at ground potential. The radioactive source was Americium 241. Negative ions created by this source were accelerated towards the positive center electrode and positive air ions moved rapidly out of the bipolar or primary ionization region. The rapid movement out of this region reduced the possibility of recombination losses and virtually makes the entire annular space a unipolar ion cloud. With a large cloud more efficient charge transfer to the particles was possible with greater instrument sensitivity and stability. Power to run the air pump and the current ammeters were both supplied by a battery thereby allowing for easy adaptability and portability in field use.

Although this invention has been described with respect to a specific embodiment for a specific use, it should be clearly apparent to those familiar with the art that other embodiments, components, uses, or variations could also be used. None of these changes should be used to limit the scope and spirit of our invention which is to be limited only by the claims which follow:

We claim:

1. A submicron particle detector comprising:

a gas tight housing having a gas inlet and outlet with a submicron charging chamber and collection electrode enclosed therein;

the charging chamber having an inner and an outer generally cylindrical shaped electrode spaced from each other and concentrically arranged with respect to each other;

said inner electrode being associated with a radioactive material, separate means for limiting the normal transmission distance of emitted radioactive particles to the volume immediately around said inner electrode to thereby cause in conjunction with the chamber's electrodes the formation of a small symmetrical bipolar region of primary ionization with a high intensity electric field thereat and also a larger unipolar charging region of lower electrical intensity between said primary ionization region and the outer electrode of the chamber;

the collection electrode being near said charging chamber and in gaseous communication to receive charged submicron particles after they past through the chamber;

pump means for moving the gas containing the submicron particles from the housing inlet to the charging chamber and then to the collection electrode; and electronic circuitry connected to both the charging chamber and collection electrode to individually measure the change in radial current flow in the charging chamber and the change in charged particle flow at the collection electrode.

2. The detector of claim 1 wherein said inner electrode is centrally located and extending longitudinally of the housing.

3. The detector of claim 1 wherein said radioactive material is embedded in and coextensive with the inner electrode.

4. The detector of claim 1 wherein said means for limiting the transmission of radioactive particles comprises a thin layer of material which encases the radioactive material and is at least several hundred times denser than the gas being pumped through the housing.

5. The detector of claim 1 wherein said formed region of primary ionization is generally cylindrical in shape around the inner electrode and has a volume less than one tenth that of the unipolar region formed between the inner electrode and outer electrode of the charging chamber.

6. A submicron particle detector comprising:

a gas tight housing having a gas inlet and outlet with a submicron charging chamber and collection electrode enclosed therein;

the charging chamber having an inner and an outer generally cylindrical shaped electrode spaced from each other and concentrically arranged with respect to each other;

said inner electrode being associated with a radioactive material having means for limiting the normal transmission distance of emitted radioactive particles to the volume immediately around said inner electrode to thereby form a small symmetrical region of primary ionization thereat when compared to a larger unipolar charging region in the chamber;

the collection electrode being near said charging chamber and in gaseous communication therewith;

a size discrimination chamber enclosed within said gas tight housing, said discrimination chamber being in gaseous communication with both said charging chamber and collection electrode having an inner and outer electrode concentrically arranged;

pump means for moving the gas containing the submicron particles from the housing inlet to the charging chamber and then to the collection electrode; and electronic circuitry connected to both the charging chamber and collection electrode to individually measure the change in radial current flow in the charging chamber and the change in charged particle flow at the collection electrode.

7. The detector of claim 6 including electrical circuitry for measuring the change in radial current flow between the size discrimination chamber's inner and outer electrodes.

8. The detector of claim 7 also including voltage varying means for changing the potential difference between the two size discrimination chamber electrodes whereby progressively larger sized submicron particles are retained in the chamber as the difference becomes greater.

9. The detector of claim 1 also including gas flow straightener means for causing the gas entering at the housing inlet to assume a generally laminar flow before entering the charging chamber.

10. The detector of claim 1 wherein there is a selfcontained portable power supply to power the detector unit including its charging chamber, collection electrode, and pump.

* * * * *